US010267785B2

(12) United States Patent
Lindsay et al.

(10) Patent No.: US 10,267,785 B2
(45) Date of Patent: *Apr. 23, 2019

(54) TRANSLOCATION OF A POLYMER THROUGH A NANOPORE

(71) Applicant: Arizona Board of Regents on behalf of Arizona State University, Scottsdale, AZ (US)

(72) Inventors: Stuart Lindsay, Phoenix, AZ (US); Peiming Zhang, Gilbert, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/922,436

(22) Filed: Mar. 15, 2018

(65) Prior Publication Data
US 2018/0209953 A1 Jul. 26, 2018

Related U.S. Application Data

(63) Continuation of application No. 14/773,072, filed as application No. PCT/US2014/020789 on Mar. 5, 2014, now Pat. No. 9,952,198.
(Continued)

(51) Int. Cl.
*G01N 33/68* (2006.01)
*G01N 33/543* (2006.01)
(Continued)

(52) U.S. Cl.
CPC ......... *G01N 33/48721* (2013.01); *C12Q 1/37* (2013.01); *G01N 15/12* (2013.01);
(Continued)

(58) Field of Classification Search
CPC .... C12Q 1/37; G01N 15/12; G01N 2333/952; G01N 2570/00; G01N 27/44704;
(Continued)

(56) References Cited

U.S. PATENT DOCUMENTS 3,619,206 A 11/1971 Lawrence et al.
4,804,707 A 2/1989 Okamoto et al.
(Continued)

FOREIGN PATENT DOCUMENTS

WO WO 1992/001476 A1 2/1992
WO 2008/092760 A1 8/2008
(Continued)

OTHER PUBLICATIONS

Bacri, L. et al. "Discrimination of neutral oligosaccharides through a nanopore", Biochemical and Biophysical Research Communications, vol. 412, No. 4, Sep. 9, 2011, pp. 561-564, DOI: 10.1016/J.BBRC.2011.07.121.
(Continued)

*Primary Examiner* — Maureen Wallenhorst
(74) *Attorney, Agent, or Firm* — Schwabe, Williamson & Wyatt, P.C.

(57) ABSTRACT

Embodiments of the present disclosure are directed to methods, systems and devices, for analyzing the molecules. For example, in some embodiments, a system is provided which includes a first volume of conducting fluid, a second volume of conducting fluid, an orifice in communication with the first and second volumes of fluid, and means for applying an electric potential difference between the first and second volumes of fluid. In some such embodiments, a conjugate product is provided which includes charged polymers each having attached thereto at least one first molecule for analysis, where the product carries a predetermined charge greater than the charge on the first molecule, and upon
(Continued)

dissolving the product in the first volume of fluid, the product is directed into the orifice.

19 Claims, 5 Drawing Sheets

Specification includes a Sequence Listing.

Related U.S. Application Data

(60) Provisional application No. 61/772,884, filed on Mar. 5, 2013.

(51) Int. Cl.
G01N 33/487 (2006.01)
G01N 27/447 (2006.01)
G01N 27/26 (2006.01)
G01N 15/12 (2006.01)
C12Q 1/37 (2006.01)

(52) U.S. Cl.
CPC . *G01N 27/44704* (2013.01); *G01N 27/44747* (2013.01); *G01N 27/44756* (2013.01); *G01N 33/5438* (2013.01); *G01N 33/6803* (2013.01); *G01N 33/6848* (2013.01); *G01N 2333/952* (2013.01); *G01N 2570/00* (2013.01); *Y10T 436/255* (2015.01)

(58) Field of Classification Search
CPC ....... G01N 27/44747; G01N 27/44756; G01N 33/48787; G01N 33/48721; G01N 33/5438; G01N 33/68; G01N 33/6818; G01N 33/6842; G01N 33/6848; G01N 33/6803; Y10T 436/143333; Y10T 436/17; Y10T 436/216; Y10T 436/24; Y10T 436/25; Y10T 436/255
USPC ..... 436/86, 89, 94, 106, 142, 149, 150, 151, 436/173, 174, 178; 422/82.01, 82.02; 435/23, 24, 287.1
See application file for complete search history.

(56) References Cited

U.S. PATENT DOCUMENTS

| | | | |
|---|---|---|---|
| 7,700,306 | B2 | 4/2010 | Thompson et al. |
| 8,003,319 | B2 | 8/2011 | Polonsky et al. |
| 8,278,055 | B2 | 10/2012 | Su et al. |
| 8,628,649 | B2 | 1/2014 | Lindsay et al. |
| 8,961,757 | B2 | 2/2015 | Nuckolls et al. |
| 8,968,540 | B2 | 3/2015 | Reinhart et al. |
| 9,140,682 | B2 | 9/2015 | Lindsay et al. |
| 9,274,430 | B2 | 3/2016 | Gyarfas et al. |
| 9,395,352 | B2 | 7/2016 | Lindsay et al. |
| 9,593,372 | B2 | 3/2017 | Lindsay et al. |
| 9,766,248 | B2 | 9/2017 | Lindsay et al. |
| 9,810,681 | B2 | 11/2017 | Lindsay et al. |
| 9,952,198 | B2 * | 4/2018 | Lindsay ........... G01N 33/48721 |
| 2006/0073489 | A1 | 4/2006 | Li et al. |
| 2007/0154890 | A1 | 7/2007 | Isobe |
| 2009/0298072 | A1 | 12/2009 | Ju |
| 2011/0204219 | A1 | 8/2011 | Stein |
| 2012/0329741 | A1 | 12/2012 | Oyelere et al. |
| 2013/0302901 | A1 | 11/2013 | Lindsay et al. |
| 2014/0174927 | A1 | 6/2014 | Bashir et al. |
| 2015/0010935 | A1 | 1/2015 | Lindsay et al. |
| 2015/0142327 | A1 | 5/2015 | Ashcroft et al. |
| 2015/0144506 | A1 | 5/2015 | Lindsay et al. |
| 2016/0018384 | A1 | 1/2016 | Lindsay et al. |
| 2016/0177383 | A1 | 6/2016 | Ashcroft et al. |
| 2016/0194698 | A1 | 7/2016 | Lindsay |
| 2016/0258925 | A1 | 9/2016 | Gyarfas et al. |
| 2016/0280723 | A1 | 9/2016 | Zhang et al. |
| 2017/0003245 | A1 | 1/2017 | Lindsay et al. |
| 2017/0016852 | A1 | 1/2017 | Lindsay et al. |
| 2017/0038369 | A1 | 2/2017 | Lindsay et al. |
| 2017/0067902 | A1 | 3/2017 | Zhang et al. |
| 2017/0137389 | A1 | 5/2017 | Zhang et al. |
| 2017/0138898 | A1 | 5/2017 | Mayer et al. |
| 2017/0204066 | A1 | 7/2017 | Lindsay et al. |
| 2017/0343558 | A1 | 11/2017 | Lindsay et al. |
| 2018/0223356 | A1 | 8/2018 | Ashcroft et al. |
| 2018/0224395 | A1 | 8/2018 | Lindsay et al. |
| 2018/0224422 | A1 | 8/2018 | Lindsay et al. |

FOREIGN PATENT DOCUMENTS

| | | | |
|---|---|---|---|
| WO | WO 2008/124706 | A2 | 10/2008 |
| WO | WO 2009/117517 | A2 | 9/2009 |
| WO | WO 2009/117522 | A2 | 9/2009 |
| WO | WO 2010/042514 | A1 | 4/2010 |
| WO | 2010/082860 | * | 7/2010 |
| WO | WO 2011/097171 | A1 | 8/2011 |
| WO | WO 2013/116509 | A1 | 8/2013 |
| WO | WO 2013/123379 | A2 | 8/2013 |

OTHER PUBLICATIONS

Biswas, Sudipta et al. "Click Addition of a DNA Thread to the N-Termini of Peptides for Their Translocation through Solid-State Nanopores", ACS NANO, vol. 9, No. 10, Sep. 12, 2015 (online), pp. 9652-9664, DOI: 10.1021/acsnano.5b04984.

Blumberg, Shmaryahu et al. "Inhibition of alpha-Chymotrypsin by D-Tryptophan Amide Covalently Bound to Macromolecular Carriers: Specific, Steric, and Electrostatic Effects", Biochemistry, vol. 18, No. 10, May 1, 1979, pp. 2126-2133, ISSN: 0006-2960, DOI: 10.1021/bi00577a044.

Gang, Wang et al. "An Integrated, Low Noise Patch-Clamp Amplifier for Biological Nanopore Applications", 32$^{nd}$ Annual International Conference of the IEEE EMBS, Buenos Aires, Argentina, Aug. 31-Sep. 4, 2010, IEEE, Piscataway, NJ, USA, Aug. 31, 2010, pp. 2718-2721, DOI: 10.1109/IEMBS.2010.5626570.

Huang, S. et al. Identifying single bases in a DNA oligomer with electron tunneling. Nature Nanotechnology 5, 868-873, Nov. 14, 2010 (online), doi:10.1038/nnano.2010.213.

Keyser, U. F. et al., "Direct force measurements on DNA in a solid-state nanopore", Nature Physics 2, 473-477 (2006), doi:10.1038/nphys344.

Koehler, C. J. et al. "Isobaric Peptide Termini Labeling Utilizing Site-Specific N-Terminal Succinylation", Analytical Chemistry 2011, 83, 4775-4781, Apr. 29, 2011.

Liang, F. et al., Synthesis, Physicochemical Properties, and Hydrogen Bonding of 4(5)-Substituted-1H-imidazole-2-carboxamide, A Potential Universal Reader for DNA Sequencing by Recognition Tunneling. Chemistry—A European Journal, vol. 18, Issue 19, Mar. 29, 2012, pp. 5998-6007, DOI: 10.1002/chem.201103306.

Mohammad, M. M. et al. "Controlling a Single Protein in a Nanopore through Electrostatic Traps", Journal of the American Chemical Society, vol. 130, No. 12, pp. 4081-4088, Mar. 6, 2008 (web), DOI: 10:1021/JA710787A.

Nivala, J. et al. "Unfoldase-mediated protein translocation through an alpha-hemolysin nanopore", Nature Biotechnology, vol. 31, No. 3, Feb. 3, 2013, pp. 247-250, DOI: 10.1038/NBT.2503.

Pang, P. et al. "Origin of Giant Ionic Currents in Carbon Nanotube Channels", ACS Nano. 2011 5(9), pp. 7277-7283, Sep. 2, 2011 (online), doi: 10.1021/nn202115s.

Thakur, S. S. et al., "Deep and Highly Sensitive Proteome Coverage by LC-MS/MS Without Prefractionation", Molecular & Cellular Proteomics, 10, M110.003699, May 17, 2011, doi: 10.1074/mcp.M110.003699.

* cited by examiner m = 1-6; k = 1-6; n = 1-300

M =1-6; n =1-300; B = any organic group

R = H, alkyl; n =1 n =1 -

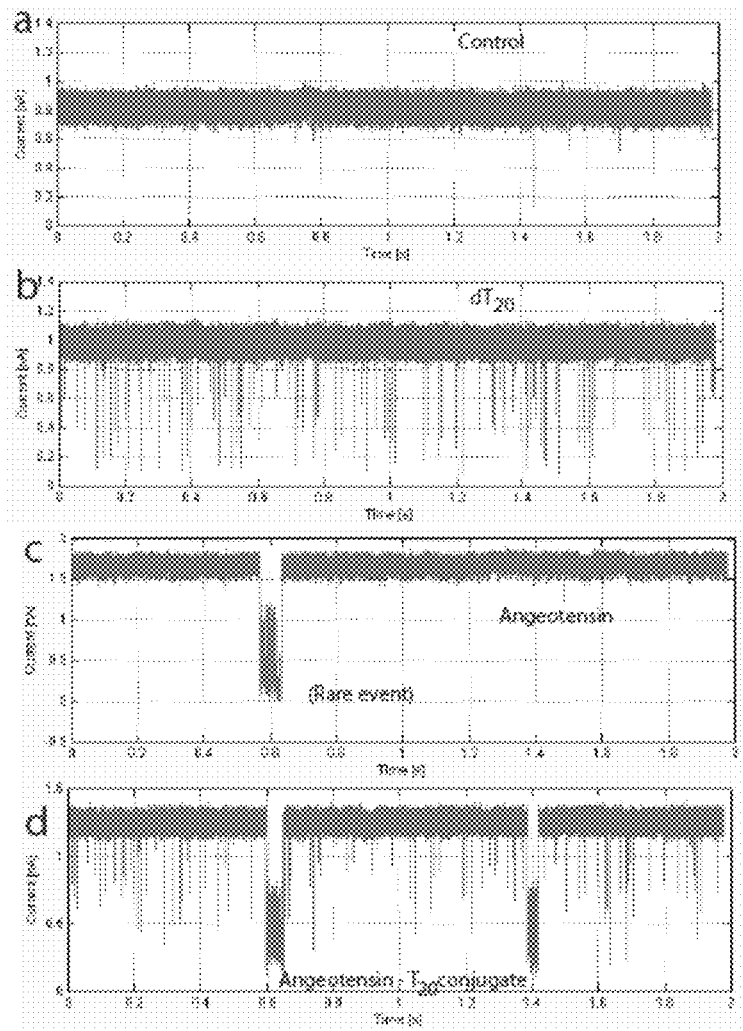
FIGURES 7a-d

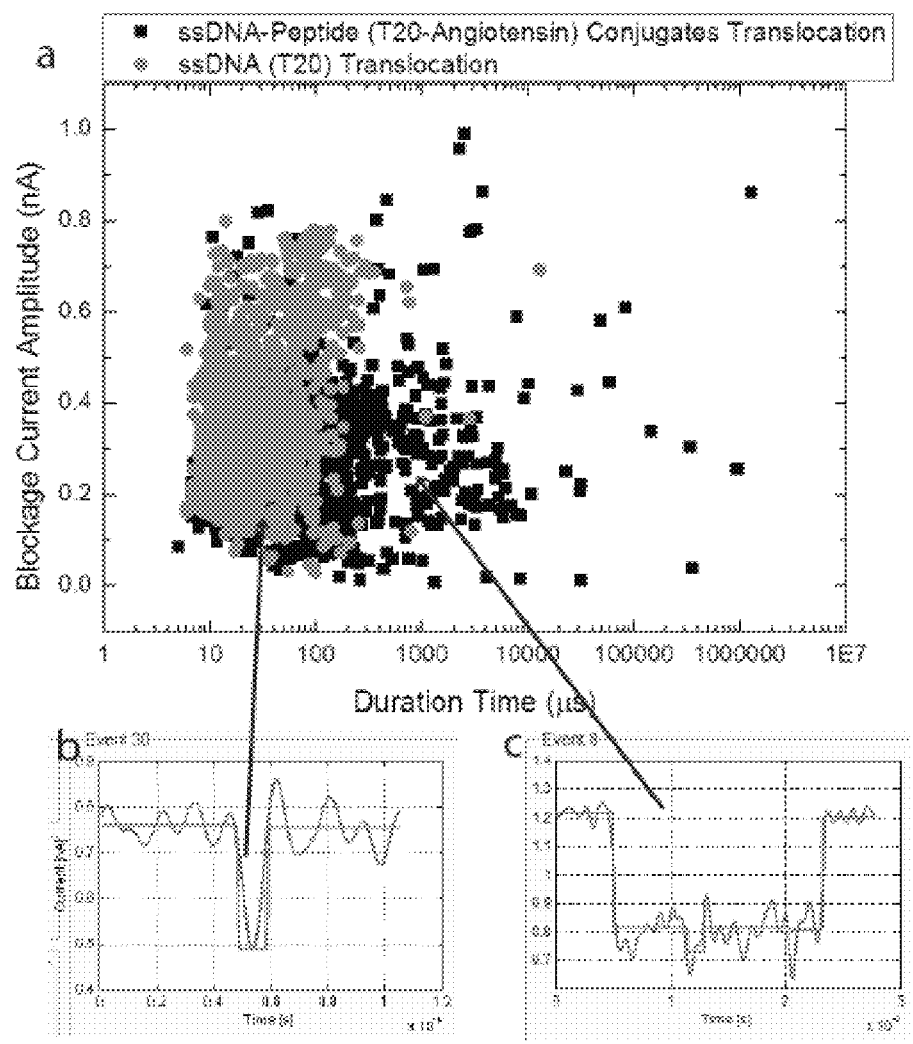
FIGURES 8a-c

TRANSLOCATION OF A POLYMER THROUGH A NANOPORE

CROSS-REFERENCE TO RELATED APPLICATIONS

This application is a continuation of U.S. patent application Ser. No. 14/773,072, filed Sep. 4, 2015, now U.S. Pat. No. 9,952,198, which is a U.S. national stage application of International Application No. PCT/US2014/020789, filed on Mar. 5, 2014, and claims benefit of and priority to U.S. Provisional Application No. 61/772,884, filed on Mar. 5, 2013. Each disclosure of which is herein incorporated by reference in its entirety.

GOVERNMENT SUPPORT

This invention was made with government support under grant number R01 HG006323 awarded by the National Institutes of Health. The government has certain rights in the invention.

INCORPORATION BY REFERENCE OF SEQUENCE LISTING

The contents of the text file named "ARIZ-010_C01US Seq Listing.txt", which was created on Mar. 14, 2018 and is 1.3 KB in size, are hereby incorporated by reference in their entireties.

BACKGROUND OF THE DISCLOSURE

The basis of some of the embodiments of the present disclosure is the trapping of target molecules by a recognition reagent (referred to as a reader molecule) tethered to tunneling electrodes, which may be referred to as recognition tunneling (or RT). In a series of earlier disclosures, WO2009/117522A2, WO2010/042514A1, WO2009/117517, WO2008/124706A2, and WO 2011/097171, each of which is incorporated herein by reference, systems and methods are disclosed where nucleic acid bases may be read by using the electron tunneling current signals generated as the nucleo-bases pass through a tunnel gap consisting of two electrodes functionalized with reader molecules. A demonstration of the ability of this system to read individual bases embedded in a polymer was given by Huang et al.[1]

RT may be also used to read an amino acid sequence, leading to protein sequencing in a nanopore/orifice, as set out in WO 2013/116509, entitled "Systems, Apparatuses And Methods For Reading an Amino Acid Sequence" ("the '509 publication"). In the '509 publication, two methods are disclosed for sequencing proteins based on recognition tunneling. In one method, an enzyme coupled to a functionalized orifice or nanopore is used to feed amino acids into a tunnel junction as they are sequentially cleaved from the end of a protein chain. The second method feeds intact peptides through a nanopore where the amino acid sequence is read out as each amino acid residue passes through the tunnel junction. In some of embodiments of the second approach, the method is simpler and more straightforward, and may be configured to produce longer sequence reads.

The '509 publication also describes methods and systems for reading negatively or positively charged peptides using a pair of nanopores—one biased to attract the positive peptides, the other biased to attract the negative peptides, and methods and systems where neutral peptides are pulled through a nanopore by electro osmosis. A possible issue with this approach is that it requires a separate arrangement for each type of net peptide charge, positive, negative and neutral. Furthermore, the approaches yield no information about which end, N or C terminus, of the peptide enters the nanopore first. Finally, the electrical force on the peptide varies with the charge on the peptide, so a significant run of neutral residues or residues of opposite charge to the overall charge of the peptide result in no force (or even a reversed force) on segments of the peptide. In fact, significant forces may be required to pull the peptide through the nanopore in order to overcome the tendency of the peptide to fold.

Accordingly, in view of the above-noted issues, it would be desirable to develop a method to draw peptides of any charge through a nanopore and to do so in a known orientation (N or C terminus first). In addition, it is desirable to exert a known force pulling on the peptide, independent of its particular charge. By means of protein expression in cells, Nivia et al.[3] have engineered proteins by fusing negatively charged peptides into their C-terminus in order to drag the protein into the nanopore, regardless of the intrinsic charge on the polymer. This procedure will not work on the naturally occurring proteins that one would wish to sequence with a nanopore. Accordingly, this disclosure provides procedures for attaching charged polymers to N termini of naturally-occurring proteins.

Additionally, the current dominant method for proteomic analysis is mass spectrometry, which typically requires as much as a microgram of protein (corresponding to 0.1 nanomoles of a 10 kD protein), though samples of several mg are required for enrichment to detect low abundance (<5%) modified sites (e.g. phosphorylation). In some RT systems for identifying amino acids (e.g., the '509 publication), sample concentrations of about 10 uM and working volumes of 0.1 ml are required, which correspond to a nanomole of sample (i.e., sample requirements are comparable to mass spectrometry). Since samples are delivered to the tunnel junction by diffusion, the quantification of mixed analytes is complicated by differential diffusion and differential binding in the junction. Accordingly, it is desirable to have a method that delivers samples to the junction in a more deterministic way, and uses lower concentrations of analyte.

At least some of these and other goals may be achieved by at least some embodiments of the present disclosure.

SUMMARY OF SOME OF THE EMBODIMENTS

Accordingly, at least some of the embodiments supported by the present disclosure address one and/or another of the issues discussed above.

In some embodiments, a device for analyzing the molecules is provided and includes a first volume of conducting fluid, a second volume of conducting fluid, an orifice in communication with said first and second volumes of fluid, and means for applying an electric potential difference between said first and second volumes of fluid. In some such embodiments, a conjugate product (which may also be referred to as product) is provided which comprises charged polymers each having attached thereto at least one first molecule for analysis, where the product carries a predetermined charge greater than the charge on the first molecule, and upon dissolving a product in the first volume of fluid, the product is directed into the orifice.

In some embodiments, a device for directing a peptide molecule for analysis into an orifice of an analysis device is provided includes a first chamber and a second chamber, where each compartment includes an electrolytic solution. The device also includes a membrane separating the second chamber from the first chamber, an orifice provided in the membrane configured to receive and/or pass a product between the first and the second chambers, a first electrode provided in the first chamber, and a second electrode provided in the second chamber. Upon the product, e.g., a conjugate product comprising a plurality of peptide fragments for analyzing, each fragment being coupled at a corresponding N-termini to a polymeric ion via a cross linker (a polymeric ion being a polymer comprising multiple charges) being dissolved in the electrolyte solution in the first chamber and a bias being applied between the first and second electrodes, the product is at least pulled into the nanopore upon the bias of the second electrode being configured to attract the polymeric ion of the product.

In such embodiments, the polymeric ion comprises repeated negative charges, and upon the first electrode being biased negative and the second electrode being biased positive, the negatively charged polymeric ions are pulled into the nanopore.

In such embodiments, upon a first electric field of a first predetermined amount being established on a first side of the nanopore and facing the first chamber, the first electric field extends a distance $\lambda$ from the nanopore, and a second electric field of a second predetermined amount is established on a second side of the nanopore facing the second chamber, the second electric field extending the distance $\lambda$, the first electric field pulls the product into the nanopore from the first chamber, and the second electric field pulls the product out of the nanopore into the second chamber.

In such embodiments, the bias may be configured such that the product does not fold. In addition, the plurality of peptide fragments may be between about 2 and about 60 peptides.

In some embodiments, a mass spectrometer configured to identify the peptide fragments may be included.

In some embodiments, the plurality of peptides may be functionalized by modifying the $\alpha$-N-terminus with succinic anhydride.

In some embodiments, a pair of orifice electrodes in communication with the orifice may be provided, where an AC voltage of at least 1 kHz in frequency is applied between the orifice electrodes.

In some embodiments, the presence of a molecule in the orifice may be detected by means of non-linear processing of the AC current signal.

In some embodiments, an electronic circuit for controlling the values of bias applied between the first electrode and the orifice electrodes and the second electrode and the orifice electrodes, where the circuit receives input from a signal generated by the orifice electrodes. The voltage applied between the orifice electrodes may comprise an AC and a DC component.

In some embodiments, a method for generating a product containing a plurality of peptide fragments for analysis is provided, and may include digesting a peptide having a plurality of lysine residues with Lys-C, trypsin, or trypsin/Lys-C, resulting in a plurality of peptide fragments, each having an $\alpha$-N-termini, wherein each peptide fragment includes a lysine at their C termini, reacting an alkyne modified succinic anhydride, 3-(2-propynyl)succinic anhydride in a sodium acetate buffered solution at a predetermined pH to selectively add alkynes to the $\alpha$-N-termini of the peptides, and attaching an azide terminated polymeric ion to each peptide by the Cu(I) catalyzed reaction of azide and alkyne.

In some embodiments, a method for directing peptide fragments of a protein into an orifice of a protein sequencing apparatus/device is provided and includes providing an apparatus/device according to any of the disclosed embodiments, digesting a protein for sequencing with endoproteinase Lys-C to produce a plurality of peptide fragments, reacting the fragments with 3-(2-propynyl)succinic anhydride at a predetermined pH in a sodium acetate buffer to produce alkyne-modified peptides, reacting a polyion polymer terminated with an azide with the alkyne-modified peptides in the presence of Cu(I), resulting in a product of polymer and alkyne-modified peptide, purifying the product on a size exclusion column, and placing the product in the first chamber of apparatus/device, where the second chamber is biased positively to draw the product through the orifice.

In some embodiments, a method of directing a polymer molecule into and/or through an orifice of a sequencing device is provided and includes attaching a charged polymer to one end of a polymer to be analyzed, resulting in a product, placing the product into a conducting solution in communication with an orifice, and applying an electrical bias across the orifice such that the charged polymer of the product is pulled into and optionally through the orifice, thereby pulling the polymer to be analyzed into and optionally through the orifice.

In such embodiments:
the polymer for analysis may be a protein;
the polymer for analysis may be a peptide; and
the polymer molecule may be an oligosaccharide.

In some embodiments, attachment between a charged polymer and the polymer for analysis is made via a succinic anhydride reaction with a terminal amine of a protein or peptide. The charged polymer may be a polymer of phosphate diesters In some embodiments, entry of the charged polymer into the orifice triggers control of the bias applied across the orifice.

In some embodiments, the polymer for analysis (i.e., an analyte) is tethered to a charged tail, such that transport into the RT junction may be dominated by the charged tail component (e.g., and not the properties of the analyte itself). Additionally, in some embodiments, operating the RT apparatus in a low salt (e.g., ≤0.2M) solution, significant count rates can be obtained with sample concentrations as low as a few picomolar (for example). Thus, for example, in 0.1 ml of solution, just a few femtomoles of sample are required, a significant improvement on mass spectroscopy (for example). Furthermore, because transport to the RT junction is deterministic (according to some embodiments), the contents of the mixture can be quantified just by counting the various types of single molecule signal. Accordingly, in such embodiments, this removes the need to enrich samples which, in mass spectrometry, can lead to as much as 20 mg (2 µmoles of a 10 kD protein) of sample being required.

In some embodiments, a method of characterizing modifications of an amino acid or protein is provided which may comprise classifying recognition tunneling signals generated by the sequential passage of molecules through a recognition tunneling junction according to whether a trained machine-learning algorithm determines each signal as a normal protein of amino acid, or as a post-translationally modified amino acid, wherein determining comprises counting the number of each type of post translational modification, and unmodified molecules. The method may also include calculating the fraction of molecules with each post translational modification determined.

In some embodiments, a series of new compounds of polyphosphate diester are presented, as set out in FIG. 5. To that end, in some such embodiments, a compound of formula (I) is presented:

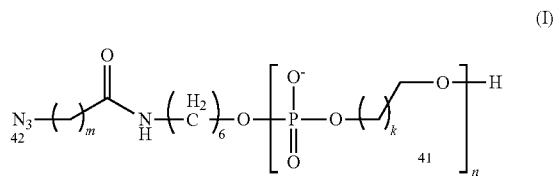

(I)

wherein m may be any of 1-6, k may be any of 1-6, and n may be any of 1-300.

In some embodiments, a compound of formula (II) is presented

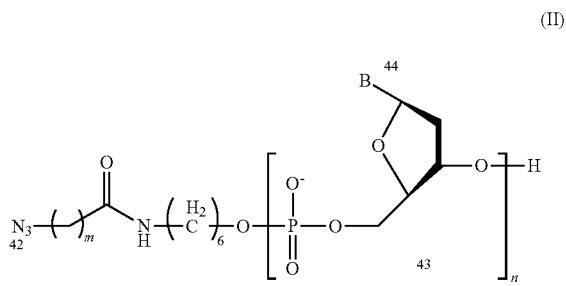

(II)

wherein m may be any of 1-6, n may be any of 1-300, and B may comprise an organic group.

These and some of the many other embodiments taught by the present disclosure will become even more evident with reference to the drawings included with the present application (a brief description which is provided below), and the detailed description which follows.

BRIEF DESCRIPTION OF THE DRAWINGS

FIG. 7a-d, illustrate blockade signals from buffer alone (a), DNA ($dT_{20}$) alone (b), angiotensin alone (c), and upon the DNA-angiotensin conjugate being added, frequent blockade signals are observed again (d), according to some embodiments of the present disclosure.

FIGS. 8a-c, illustrate (a) scatter plot of blockade time and blockade amplitude for ssDNA alone (gray) and the angiotensin-DNA conjugate (black); (b) and (c) show examples of signals (curved traces) as fitted to obtain amplitudes and widths (block traces), according to some embodiments of the present disclosure.

DETAILED DESCRIPTION OF SOME OF THE EMBODIMENTS

It is an object of at least some of the embodiments of the present disclosure to provide a system and method to draw peptides of any charge into and/or through a nanopore (the term nanopore and orifice used interchangeably throughout this disclosure) and to do so in a known orientation (N or C terminus first). In addition, it is an object of at least some of the embodiments of the present disclosure to exert a known force to pull on the peptide, independent of its particular charge. These and other goals are achieved by at least some of the embodiments of the present disclosure.

Figure 1:
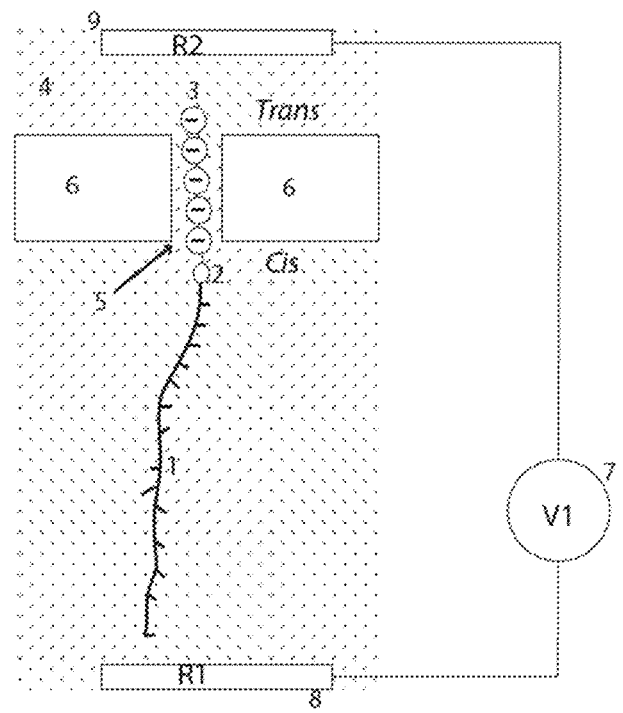
FIG. 1 is an illustration showing how a charged polymer tethered to a peptide of arbitrary charge is used to feed the peptide into a nanopore according to some embodiments of the present disclosure.

Accordingly, some of the embodiments of the present disclosure are outlined schematically in FIG. 1. As shown, in some embodiments, peptide fragments 1, obtained by enzymatic digestion of the protein to be sequenced (for example), are coupled at their N-terminus by means of a cross linker 2 to a polymeric ion 3 chosen to carry much larger charge than any of the protein fragments. Thus, if a typical fragment size is between about 10 to about 100 amino acids in length, the polymeric ion 3 would be at several tens to several hundred of units in length, so as to be longer than the peptide fragments. With the length (and hence charge) of the polymeric ion being greater than the length (and thus maximum possible charge) of the peptide fragment, the net charge of the system of peptide fragment 1, cross linker 2, and polymeric ion 3 is determined by the polymeric ion. When the conjugate (1-2-3) is dissolved in an electrolyte solution 4 contained in two compartments (labeled cis and trans) separated by a nanopore 5 in a membrane 6 (that separates the two compartments), and a bias V1 (7) is applied between a reference electrode in the cis compartment, R1 (8) and a reference electrode in the trans compartment, R2 (9), the conjugate (1-2-3) will be pulled into the nanopore if the bias of R2 (9) is such as to attract the polymeric ion. For example, if the polymeric ion consists of repeated negative charges, such as phosphate ions, then R1 will be biased negative, and R2 biased positive to pull the negative polymeric ion into the pore.

Figure 2:
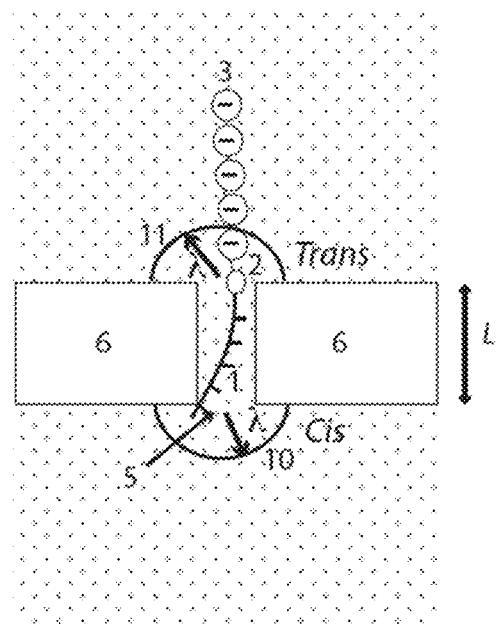
FIG. 2 is an illustration showing regions of high electric fields at the entry and exit of the nanopore and how they interact with the charged polymer, according to some embodiments of the present disclosure.

In some embodiments, the motion of the peptide section to be sequenced depends on the pore geometry, as illustrated in FIG. 2. Specifically, regions of high electric field are confined to the ends of the nanopore and are shown extending a distance λ from the end of the nanopore. λ is somewhat salt-dependent, varying between about 10 nm at 0.01M salt and 5 nm at 1M salt (see calculation shown in Figure S22 of Peng et al.[4]). Accordingly, in some embodiments, the charged polymer is pulled into the pore from the cis side by the high field region on this side, 10, and pulled out again by the high field region on the trans side, 11. Thus, in such embodiments, the polymeric ion 3 is drawn into the pore and then out again. In some embodiments, the force on the polymer is independent of pore and polymer length, depending only on the potential difference applied across the pore. For example, for a DNA polymeric ion, the force generated is 0.24 pN/mV (see paper by Keyser et al.[5]). Since the force to unfold a single IgG domain (an example of a tightly folded protein) is in the range of about 5 to about 40 pN, a bias across the pore of just 170 mV is adequate to overcome peptide folding, pulling the peptide into the pore as a linear structure (according to some embodiments).

In some embodiments, the pore length, L, is typically about 20 nm, long enough to contain about 40 peptide residues (of about 0.5 nm residue-to-residue spacing). The polymeric ion 3 thus controls the motion of the peptide over a distance of about L+λ. For example, in the case where L is 20 nm and λ=5 nm, together equal to 25 nm corresponding to about 50 amino acid residues. Once the polymeric ion has passed out of the high field region, subsequent transport (of an uncharged peptide) is dominated by diffusion, a much slower process. Thus, in a typical nanopore with dimensions given above, active electric field control of translocation is limited to no more than about 50 amino acid residues. Accordingly, in some embodiments, this is adequate for "Bottom Up" protein identification by mass spectrometry.[6] In such a case, the polymeric ion 3 is at least 100 units in length to guarantee that the total charge of the assembly was completely dominated by the polymeric ion. In some embodiments, a longer nanopore channel length (L in FIG. 2) and a longer polymeric ion allow longer peptide fragments to be pulled through the pore. For example, the largest IgG domain is about 110 amino acids, requiring a pore length of about 50 nm and a polymeric ion of about 200 charged units in length.

In order to connect a polymeric ion to a peptide fragment, it is necessary to selectively functionalize an end of the peptide without modifying the side chains. This can be done using modification of the α-N-terminus with succinic anhydride. When this reaction is carried out is sodium acetate buffer at pH 7.6, the N-terminus may be modified while lysines (the only other charged primary amines among the naturally occurring amino acid residues) are left unmodified.[7] It is helpful to increase the density of accessible N-termini relative to lysine residues because the probability of an unwanted reaction with the primary amine in lysine residues will increase as the number of lysine residues in a protein molecule. Accordingly, the specificity of the reaction is increased by cutting the protein into fragments containing only one lysine residue each. This is readily achieved using endoproteinase such as Lys-C.[7]

Figure 3:
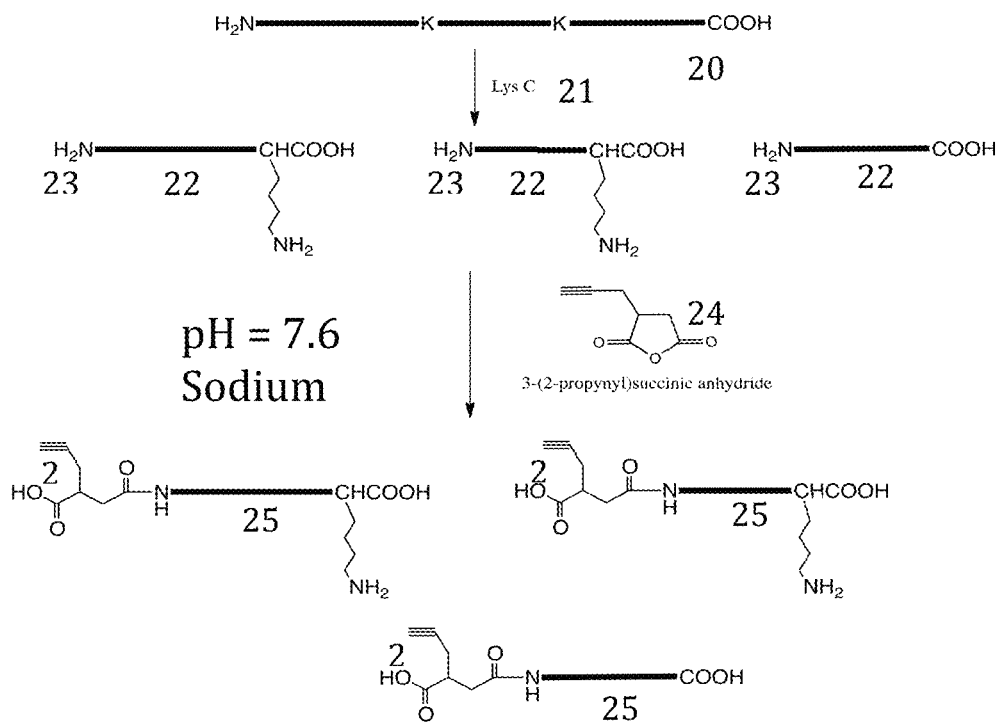
FIG. 3 illustrates selective functionalization of the N-terminus of the peptide fragments according to some embodiments of the disclosure, where selectivity may be enhanced by digesting the protein into fragments containing only one lysine residue.
Figure 4:
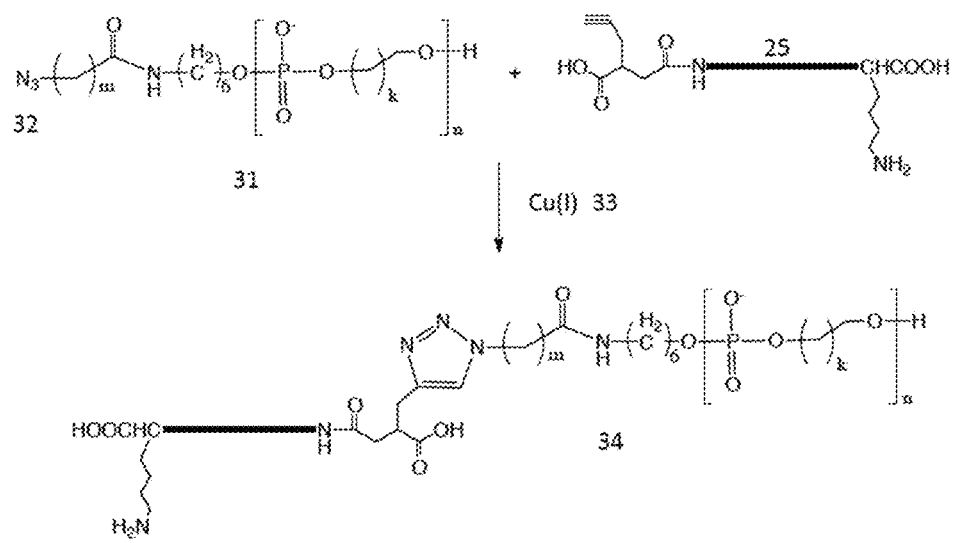
FIG. 4 illustrates covalent conjugation of the functionalized protein fragments with a polymeric ion according to some embodiments of the present disclosure.

A coupling process is illustrated in FIGS. 3 and 4. As an example, a peptide containing two lysine residues ("K") is shown (20). The thick solid bar represents other residues in the peptide. Digestion with Lys-C (21) produces three fragments (22), only two of which contain one lysine in their respective sequences and the rest contains no lysine. Although presenting three N-termini (23), it reduces the possibility for unwanted reactions from lysines. An alkynylated succinic anhydride, 3-(2-propynyl)succinic anhydride (24) is used to selectively add alkynes (26) to the N-termini of the peptides (25) in the sodium acetate buffered solution at pH 7.6. An azide terminated polymeric ion is attached to the peptide by the Cu(I) catalyzed reaction of azide and ethyne well known in the art (i.e., "click" chemistry), which is illustrated in FIG. 4. Here the polymeric ion is shown as a generic polyphosphate diester (31) terminated with an azide moiety (32). Reaction with the alkynylated peptide 25 fragments in the presence of a Cu(I) catalyst (33) produces the concatenated molecule (34). In this case, the peptide is coupled to the polymeric ion at its N-terminus, and this is the end that will be threaded into the nanopore first, achieving the goal of orienting the peptide for a sequence read.

Figure 5:
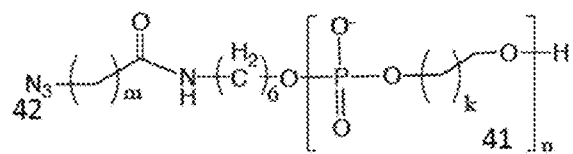
FIG. 5 illustrates examples of polymeric ions suitable for conjugation with functionalized peptides according to some embodiments of the present disclosure.
Figure 5:
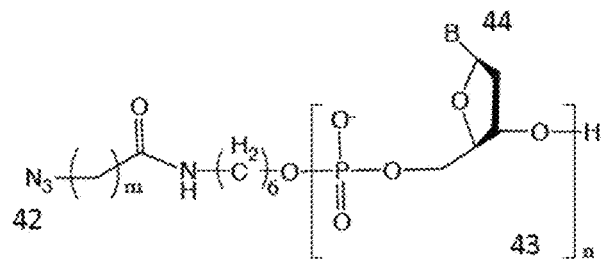
Figure 6:
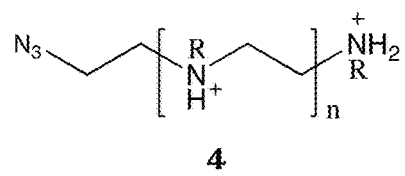
FIG. 6 illustrates examples of a polycation, including azido polyethylenimine and azido polylysine, according to some embodiments of the present disclosure.
Figure 6:
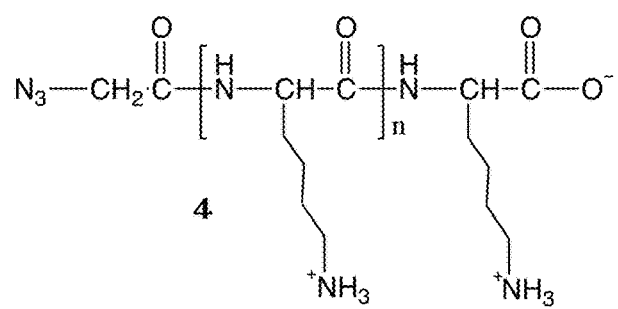

Examples of suitable polyanions are shown in FIG. 5. The simplest diester consists of a chain of phosphates (41) linked by k repeats of methylene groups (k=1 to 6 are reasonable values, both easy to synthesize and soluble in aqueous buffer). The polyanion is terminated in an azide 42 linked by m repeated methylene units where m=1 to 6. In another embodiment, the polymer repeat (43) includes a sugar with an organic residue B (44) (for example DNA where B could be the T base). Using a simple phenol group for B may ensure no hydrogen bonding, and thus, no recognition tunneling signals. However, the use of a DNA base would generate recognition tunneling signals ahead of the peptide signals, and may prove useful for calibrating the readout. The polymer is again terminated in an azide (42). By the same token, a polycation such as azido polyethylenimine (45) and azido polylysine (46) (FIG. 6) can be used for the translocation. In this case, the polarity of the electrodes would be reversed so that the cargo to be analyzed would be pulled towards the negative electrode.

In some embodiments, the method for sequencing a protein includes two or more of the following steps (and in some embodiments, all steps):
 the protein to be sequenced is digested with endoproteinase Lys-C, and/or trypsin;
 the resulting fragments are reacted with 3-(2-propynyl) succinic anhydride at pH 7.6 or below in a sodium acetate buffer;
 a polyion polymer terminated with an azide reacts with the alkyne-modified peptides in the presence of Cu(I);
 the conjugate product (polymer ion+peptide) is purified on a size exclusion column; and
 the polyion labeled peptide mix is placed in the cis chamber of a nanopore apparatus/device, and the trans chamber is biased positively to draw the concatenated polymers through the nanopore;

In some embodiments, the tunneling signal generated by the polymeric ion provides an advance notice of the arrival of the following peptide chain and can be used to activate control circuitry as described below. It will be recognized that a similar approach could be used to pull other polymers (such as poly saccharides) through nanopores for sequencing. In the case of polysaccharides, specific terminal functionalization at a terminal —OH group may be unlikely to be successful because of the —OH groups in the sugars. However, the additional step of separating end-functionalized molecules by chromatography may be used to address this.

In some embodiments, azidoacetic anhydride can be used as a substituent of 3-(2-propynyl)succinic anhydride. Preparation of azidoacetic anhydride (Scheme 1):

Scheme 1

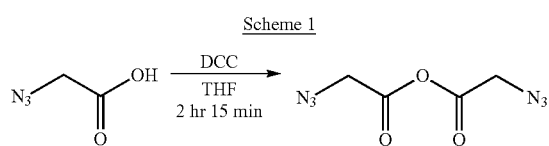

N,N'-Dicyclohexylcarbodiimide (DCC, 204 mg, 0.98 mmol) was added to a solution of 2-azidoacetic acid (200 mg, 1.9 mmol) in anhydrous tetrahydrofuran. The mixture was stirred for 2 hr and 15 min, filtered. The filtrate was concentrated by rotary evaporation, furnishing azidoacetic anhydride (150 mg, 42%) as a colorless liquid. $^1$H NMR (400 MHz, CDCl$_3$): δ=3.85 (s, 4H); $^{13}$C NMR (100 MHz, CDCl$_3$): δ=168.3, 50.0 ppm.

Example: Reaction of Azidoacetic Anhydride with a Peptide Bearing One Lysine (Scheme 2)

Scheme 2

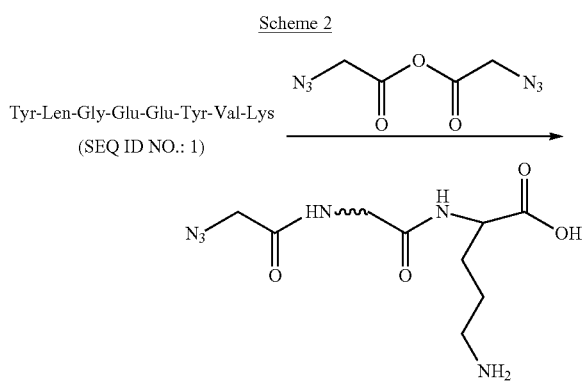

Tyr-Len-Gly-Glu-Glu-Tyr-Val-Lys
(SEQ ID NO.: 1)

A solution of azidoacetic anhydride (1 mM, 15 μL) in acetonitrile was added to the peptide solution (50 μM, 15 μL) in a sodium acetate buffer (50 mM, pH 6.7) in an eppendorf tube at 0° C. Before the addition, both azidoacetic anhydride and peptide solutions were cooled at 0° C. for 10 min. After 30 min, MALDI-TOF mass spectrometry showed that the peptide starting material was consumed and a new product produced. The product was characterized as an azidoacetyl mono substituted peptide by MALDI mass: m/z (M+H) calculated: 1083.12; found: 1083.33.

Example: Control Study (Scheme 3)

Scheme 3

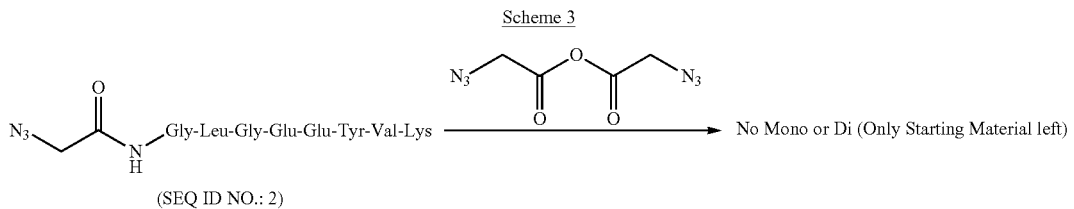

Gly-Leu-Gly-Glu-Glu-Tyr-Val-Lys → No Mono or Di (Only Starting Material left)

(SEQ ID NO.: 2)

To demonstrate that the reaction selectively takes place at the N terminus, the same peptide with N-terminus blocked by an azidoacetyl group reacted with azidoacetic anhydride under the exactly same conditions. MALDI mass spectrometry showed that no reaction took place even after 40 min. This confirmed that azidoacetylation was occurring only at the N-terminus of the peptide.

Example: Reaction of Azidoacetic Anhydride with a Peptide Sequence Having Three Lysines (Scheme 4)

Scheme 4

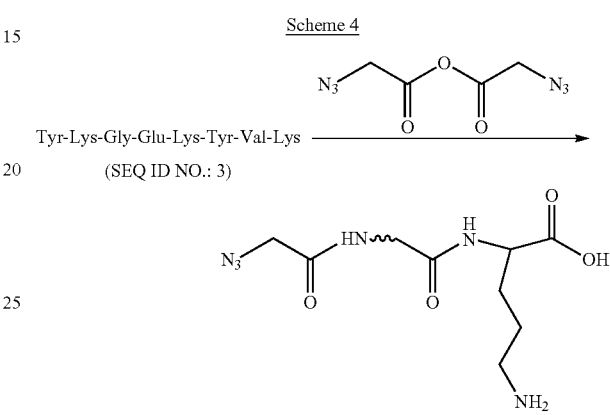

Tyr-Lys-Gly-Glu-Lys-Tyr-Val-Lys
(SEQ ID NO.: 3)

A solution of azidoacetic anhydride (1 mM, 15 μL) in acetonitrile was added to the peptide solution (50 μM, 15 μL) in a sodium acetate buffer (50 mM, pH 6.7) in an eppendorf tube at 0° C. Before the addition, both azidoacetic anhydride and peptide solutions were cooled at 0° C. for 10 min. After 20 min, MALDI-TOF mass spectrometry showed that the peptide starting material was consumed and a new product produced. The product was characterized as an azidoacetyl mono substituted peptide by MALDI mass: m/z (M+H) calculated: 1097.17; found: 1097.45.

Example: Control Study (Scheme 5)

Scheme 5

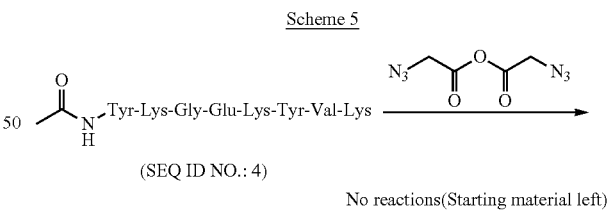

(SEQ ID NO.: 4)

No reactions(Starting material left)

The same peptide with N-terminus blocked by an acetyl group reacted with azidoacetic anhydride under the exactly same conditions. MALDI mass spectrometry showed that no reaction took place even after 45 min. This confirmed that azidoacetylation was occurring only at the N-terminus of the peptide.

Example: Synthesis of an Angiotensin I and PolyT$_{20}$ Conjugate

A. Modification of Angiotensin I Using Azidoacetic Anhydride (Scheme 6):

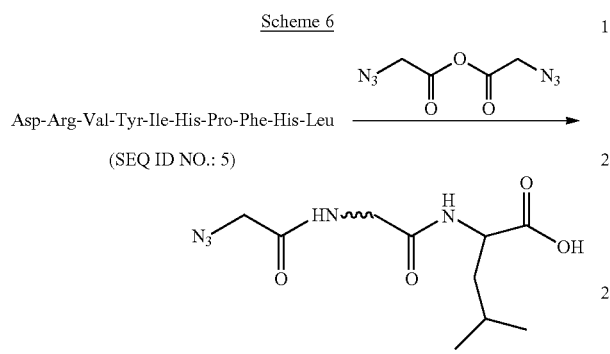

Scheme 6

Asp-Arg-Val-Tyr-Ile-His-Pro-Phe-His-Leu (SEQ ID NO.: 5)

Angiotensin I (50 μM, 15 μL) in a sodium acetate buffer (50 mM, pH 6.7) was added to a solution of azidoacetic anhydride (1 mM, 15 μL) in acetonitrile in an eppendorf tube at 0° C. Before the addition, both azidoacetic anhydride and peptide solutions were cooled at 0° C. for 10 min. After 15 min, MALDI mass spectrometry showed that the angiotensin was consumed and a new product produced. The solvent was removed using SpeedVac and the residue was redissolved in of TEAA buffer (pH 7, 10 uL). The product was purified by reverse phase HPLC in a Zorbax Eclipse Plus C18 column (4.6×150 mm, particle size 5 μm) with an acetonitrile gradient of 0 to 70% over a period of 30 min (solvent A: 0.1 M TEAA buffer, pH 7.0; solvent B: acetonitrile). The major fraction at the retention time of 16.5 min was collected and lyophilized. MALDI-TOF mass spectrometry showed that it was an azidoacetyl mono substituted peptide product. The m/z (M+H) calculated: 1379.54; found: 1379.66.

B. Modification of Poly T$_{20}$ by DBCO (Scheme 7):

Scheme 7

Poly T$_{20}$-NH$_2$ +

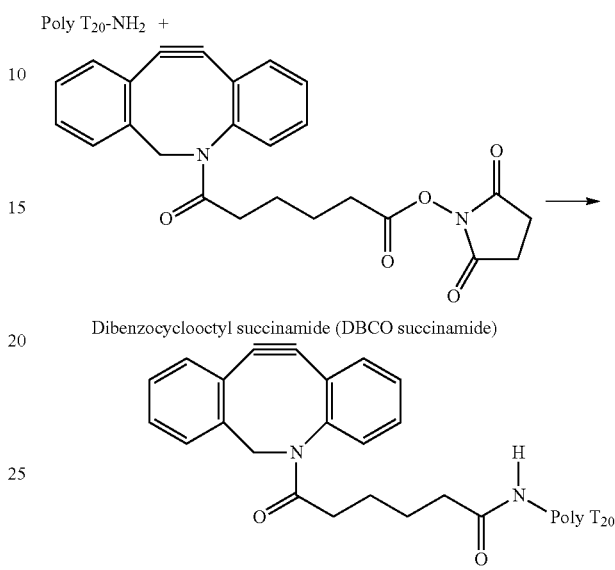

Dibenzocyclooctyl succinamide (DBCO succinamide)

An oligonucleotide Poly T$_{20}$ with a C12 amino Modifier at its 5' end (1 mM, 10 μL) in water was added into a Phosphate buffer (30 μL, pH 8.5). To this solution was added a solution of DBCO-NHS ester in DMSO (15 mM, 40 μL), which was shaken for 30 min at room temperature, followed by another addition of the DBCO-NHS ester (40 μL). The reaction mixture was shaken for additional 1.5 h. The product was purified by reverse phase HPLC in a Zorbax Eclipse Plus C18 column (4.6×150 mm, particle size 5 μm) with an acetonitrile gradient of 0 to 60% over a period of 25 min (solvent A: 0.1 M TEAA buffer, pH 7.0; solvent B: acetonitrile) and characterized by MALDI-MS. The m/z (M+H) calculated 6667.23; found: 6676.34.

C. Coupling of Poly T$_{20}$ to Angiotensin I by the Click Reaction (Scheme 8).

Scheme 8

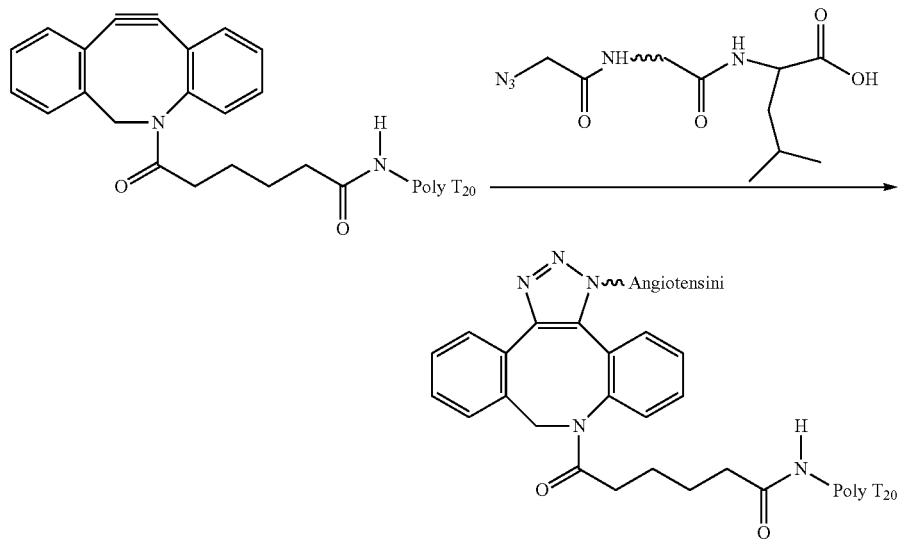

A solution of the azido modified peptide (30 µM, 15 µL) in the TEAA buffer (50 mM, pH 7) was added to a solution of the DBCO functionalized PolyT$_{20}$ (5 µM, 10 µL)) in the TEAA buffer (50 mM, pH 7), shaken at room temperature for 3 hours. The product was purified employing reverse phase HPLC in a Zorbax Eclipse Plus C18 column (4.6×150 mm, particle size 5 µm) with an acetonitrile gradient of 0 to 60% over a period of 25 min (solvent A: 0.1 M TEAA buffer, pH 7.0; solvent B: acetonitrile). The product had a retention time of 5.4 min. and characterized by MALDI-MS (m/z (M+H) of the product calculated: 7994.12; found: 7996.15). After lyophilization, the product was given as a white powder.

Demonstration of Translocation of the Peptide-DNA Complex Through a Nanopore.

FIGS. 7a-d show example ion-current blockade signals from samples which demonstrate how conjugation of the angiotensin peptide with a negatively charged PolyT$_{20}$ ssDNA results in the peptide being pulled through a 3 nm diameter nanopore, according to some embodiments. FIG. 7a shows a control signal obtained in the salt solution alone (0.4 M KCl with 10 mM Tris buffer, pH=7.0). The bias across the nanopore was 400 mV. On adding 1 uM PolyT$_{20}$ ssDNA, frequent current blockades are observed (FIG. 7b). On rinsing, the signal returns to the featureless control signal (see FIG. 7a). When 1 uM angiotensin is added, blockades are observed only occasionally (FIG. 7c). However, when the conjugated product (Scheme 8, above) is added (concentration about 1 uM), frequent blockade signals are observed (FIG. 7d). Signals from the conjugated product are distinctive, having a slightly smaller blockade amplitude and considerably longer duration than blockades owing to the ssDNA alone (FIG. 8a). Examples of fitted blockade signals are given for the ssDNA in FIG. 8b and for the angiotensin-DNA conjugate in FIG. 8c.

Thus, in some embodiments, a peptide or amino acid may be linked to a charged tail. In such embodiments, a tail comprising charged amino acids (see also, Scheme 8, infra, a charged tail linked to a single-stranded DNA, e.g., a 20 nucleotide oligothymine, T$_{20}$. Thus, in some embodiments, neutral analytes can be added to a threader molecule carrying substantial charge (e.g., 20 negative charges), so long as a terminal amine is available for the attachment chemistry (for example).

Accordingly, this may bring about a significant reduction in the amount of analyte, and concentration of analyte, required. While neutral molecules, such as polyethylene glycol and oligosaccharides, have been translocated through nanopores, mM concentrations were necessary to achieve a count rate of a few counts per second. In sharp contrast, and for example, in low salt concentrations (e.g., ≤0.2M), similar count rates were achieved for small DNA molecules at concentrations as low as, for example, 4 pM. This may be because the electric field gradient near the nanopore can collect charged molecules from a large volume of sample space.

Example: an analyte containing a terminal amine, is modified with azidoacetic anhydride to produce an azide termination. This molecule is then reacted with a charged polymer (a DNA oligomer in the preferred embodiment) that is coupled to DBCO (scheme 8). The product of this reaction is then placed in a chamber on one side (by convention, the cis side) of a nanopore articulated with a recognition-tunneling junction in a concentration that can be as low as 1 pM (for example). A positive bias of +300 to +400 mV with respect to a reference electrode on the cis side is applied to a reference electrode on the opposite (trans) side. The charged polymer is carried through the nanopore by electrophoresis, thereby pulling the analyte with it. The recognition-tunneling junction may then generate a signal characteristic of the charged polymer, which may be followed by a signal characteristic of the analyte. Thus, according to some embodiments (an example of which is immediately above), a neutral analyte, which would normally have to present at mM concentration to be translocated at rate>1 count per second, may be translocated and analyzed at a count rate>count per second with concentrations as low as 1 pM.

Various implementations of the embodiments disclosed, in particular at least some of the processes discussed, may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

Such computer programs (also known as programs, software, software applications or code) include machine instructions for a programmable processor, for example, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor and the like) for displaying information to the user and a keyboard and/or a pointing device (e.g., a mouse or a trackball) by which the user may provide input to the computer. For example, this program can be stored, executed and operated by the dispensing unit, remote control, PC, laptop, smart-phone, media player or personal data assistant ("PDA"). Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Certain embodiments of the subject matter described herein may be implemented in a computing system and/or devices that includes a back-end component (e.g., as a data server), or that includes a middleware component (e.g., an application server), or that includes a front-end component (e.g., a client computer having a graphical user interface or a Web browser through which a user may interact with an implementation of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system according to some such embodiments described above may include clients and servers. A client and server are generally remote from each other and typically interact through a communication network. The relationship of client and server arises by virtue of computer programs running on the respective computers and having a client-server relationship to each other.

Any and all references to publications or other documents, including but not limited to, patents, patent applications, articles, webpages, books, etc., presented anywhere in the present application, are herein incorporated by reference in their entirety.

Although a few variations have been described in detail above, other modifications are possible. For example, any logic flows depicted in the accompanying figures and/or described herein do not require the particular order shown, or sequential order, to achieve desirable results. Other implementations may be within the scope of at least some of the following exemplary claims.

As noted elsewhere, these embodiments have been described for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, systems and apparatuses/devices which may further include any and all elements from any other disclosed methods, systems, and devices, including any and all elements corresponding to translocation control. In other words, elements from one or another disclosed embodiments may be interchangeable with elements from other disclosed embodiments. In addition, one or more features/elements of disclosed embodiments may be removed and still result in patentable subject matter (and thus, resulting in yet more embodiments of the subject disclosure). Also, some embodiments correspond to systems, devices and methods which specifically lack one and/or another element, structure, and/or steps (as applicable), as compared to teachings of the prior art, and therefore represent patentable subject matter and are distinguishable therefrom.

REFERENCES

1 Huang, S. et al. Identifying single bases in a DNA oligomer with electron tunneling. *Nature Nanotechnology* 5, 868-873 (2010).
2 Liang, F., Li, S., Lindsay, S. & Zhang, P. Synthesis, Physicochemical Properties, and Hydrogen Bonding of 4(5)-Substituted-1H-imidazole-2-carboxamide, A Potential Universal Reader for DNA Sequencing by Recognition Tunneling. *Chemistry—a European Journal* 18, 5998-6007 (2012).
3 Nivaia, J., Marks, D. B. & Akeson, M. Unfoldase-mediated protein translocation though an alpha-hemolysin pore. *Nature Biotechnol.* 31, 247-250 (2013).
4 Pang, P., He, J., Park, J. H., Krstic, P. S. & Lindsay, S. Origin of Giant Ionic Currents in Carbon Nanotube Channels. *ACS Nano* 5, 7277-7283 (2011).
5 Keyser, U. F. et al. Direct force measurements on DNA in a solid-state nanopore. *Nature Physics* 2, 473-477 (2006).
6 Thakur, S. S. et al. Deep and Highly Sensitive Proteome Coverage by LC-MS/MS Without Prefractionation. *Molecular & Cellular Proteomics* 10, M110.003699-003691-M003110.003699-003699. (2011).
7 Koehler, C. J., Arntzen, M. Ø., Strozynski, M., Treumann, A. & Thiede, B. Isobaric Peptide Termini Labeling Utilizing Site-Specific N-Terminal Succinylation. *Analytical Chemistry* 83, 4775-4781 (2011).

What is presently claimed is:

1. A molecule directing device for directing an oligosaccharide for analysis into an orifice, the device comprising:
   a first chamber and a second chamber, wherein each chamber includes an electrolytic solution, wherein:
      the electrolytic solution in the first chamber includes a dissolved product comprising a plurality of oligosaccharides, and
      each oligosaccharide is coupled to a polymeric ion via a cross linker;
   a membrane separating the second chamber from the first chamber;
   an orifice in the membrane and configured to receive and pass each oligosaccharide between the first and the second chambers;
   a first electrode in the first chamber; and
   a second electrode in the second chamber, wherein each oligosaccharide is directed into the orifice by applying an electrical potential between the first and second electrodes; and
   a pair of orifice electrodes in communication with the orifice, wherein an AC voltage of at least about 1 kHz in frequency is applied between the orifice electrodes.

2. The device of claim 1, wherein the presence of an oligosaccharide in the orifice is detected by means of non-linear processing of an AC current signal.

3. The device of claim 1, further comprising an electronic circuit for controlling values of bias applied between the first electrode and the orifice electrodes and the second electrode and the orifice electrodes, wherein the circuit receives input from a signal generated by the orifice electrodes.

4. The device of claim 1, wherein the voltage applied between the orifice electrodes comprises an AC and a DC component.

5. The device of claim 1, wherein the polymeric ion comprises repeated negative charges such that when the first electrode is biased negative and the second electrode is biased positive, the polymeric ion is pulled into the orifice.

6. The device of claim 1, wherein:
   a first electric field of a first predetermined amount is established on a first side of the orifice facing the first chamber and extends a distance $\lambda$ from the orifice;
   a second electric field of a second predetermined amount is established on a second side of the orifice facing the second chamber and extends the distance $\lambda$; and
   the first electric field pulls the product into the orifice from the first chamber, and the second electric field pulls the product out of the orifice into the second chamber.

7. The device of claim 1, wherein the electrical potential is configured such that the product does not fold when it is directed through the orifice.

8. The device of claim 1, wherein the electrolytic solution in the first chamber comprises a salt solution of less than about 1M concentration.

9. The device of claim 1, wherein the electrolytic solution in the second chamber comprises a salt solution.

10. A method of directing peptide fragments of a protein into an orifice of a sequencing device, wherein the sequencing device comprises: (a) a first chamber and a second chamber; (b) a membrane separating the second chamber from the first chamber; (c) the orifice in the membrane; (d) a first electrode in the first chamber; and (e) a second electrode in the second chamber,
   the method comprising:
      digesting the protein to produce a plurality of peptide fragments;
      attaching a polymeric ion to the N-terminus of each peptide fragment via a cross linker to produce a conjugate product;

placing the conjugate product into an electrolytic solution in the first chamber; and applying an electrical potential between the first and second electrodes, thereby directing the conjugate product into the orifice.

11. The method of claim 10, wherein the protein is digested by endoproteinase, Lys-C, trypsin, or Lys-C/trypsin.

12. The method of claim 10, wherein each peptide fragment is functionalized by modifying the N-terminus with succinic anhydride.

13. The method of claim 12, further comprising reacting each peptide fragment with 3-(2-propynyl)succinic anhydride at a predetermined pH in a buffered solution to produce an alkyne-modified peptide, and reacting a polyion polymer terminated with an azide with the alkyne-modified peptide in the presence of Cu(I).

14. The method of claim 10, wherein each peptide fragment is functionalized by modifying the N-terminus with azidoacetic anhydride.

15. The method of claim 14, further comprising reacting each peptide fragment with azidoacetic anhydride at a predetermined pH in a sodium acetate or other buffered solution to produce an azide-modified peptide, and reacting a polyion polymer terminated with a cyclooctyne or its derivative with the azide-modified peptide in the absence of Cu(I).

16. The method of claim 10, wherein the device further comprises a pair of orifice electrodes in communication with the orifice, the method further comprising applying an AC voltage of at least about 1 kHz in frequency between the orifice electrodes.

17. The method of claim 10, further comprising detecting the presence of each peptide fragment in the orifice by means of non-linear processing of an AC current signal.

18. The method of claim 10, wherein the electrolytic solution in the first chamber comprises a salt solution of less than about 1M concentration.

19. The method of claim 10, wherein the second chamber comprises a salt solution.

* * * * *

SEQUENCE LISTING

```
<160> NUMBER OF SEQ ID NOS: 5

<210> SEQ ID NO 1
<211> LENGTH: 8
<212> TYPE: PRT
<213> ORGANISM: Artificial Sequence
<220> FEATURE:
<223> OTHER INFORMATION: Artificial Polypeptide

<400> SEQUENCE: 1

Tyr Leu Gly Glu Glu Tyr Val Lys
1               5

<210> SEQ ID NO 2
<211> LENGTH: 8
<212> TYPE: PRT
<213> ORGANISM: Artificial Sequence
<220> FEATURE:
<223> OTHER INFORMATION: Artificial Polypeptide

<400> SEQUENCE: 2

Gly Leu Gly Glu Glu Tyr Val Lys
1               5

<210> SEQ ID NO 3
<211> LENGTH: 8
<212> TYPE: PRT
```

```
<213> ORGANISM: Artificial Sequence
<220> FEATURE:
<223> OTHER INFORMATION: Artificial Polypeptide

<400> SEQUENCE: 3

Tyr Lys Gly Glu Lys Tyr Val Lys
1               5

<210> SEQ ID NO 4
<211> LENGTH: 8
<212> TYPE: PRT
<213> ORGANISM: Artificial Sequence
<220> FEATURE:
<223> OTHER INFORMATION: Artificial Polypeptide

<400> SEQUENCE: 4

Tyr Lys Gly Glu Lys Tyr Val Lys
1               5

<210> SEQ ID NO 5
<211> LENGTH: 10
<212> TYPE: PRT
<213> ORGANISM: Artificial Sequence
<220> FEATURE:
<223> OTHER INFORMATION: Artificial Polypeptide

<400> SEQUENCE: 5

Asp Arg Val Tyr Ile His Pro Phe His Leu
1               5                   10
```